United States Patent [19]
Doehner, Jr.

[11] Patent Number: 5,227,491
[45] Date of Patent: Jul. 13, 1993

[54] PROCESS FOR THE PREPARATION OF DIALKYL 2,3-PYRIDINEDICARBOXYLATE AND DERIVATIVES THEREOF FROM AN α,β-UNSATURATED OXIME AND AN AMINOBUTENEDIOATE

[75] Inventor: Robert F. Doehner, Jr., East Windsor, N.J.

[73] Assignee: American Cyanamid Company, Stamford, Conn.

[21] Appl. No.: 849,117

[22] Filed: Mar. 10, 1992

[51] Int. Cl.$^5$ ........................................ C07D 213/803
[52] U.S. Cl. ................................................. 546/250
[58] Field of Search ........................................ 540/250

[56] References Cited

U.S. PATENT DOCUMENTS 4,758,667 7/1988 Szczepanski ........................ 546/167
4,766,218 8/1988 Maulding ............................. 546/170
4,798,619 1/1989 Los ......................................... 71/66

FOREIGN PATENT DOCUMENTS

0308084-A1 3/1989 European Pat. Off. ............ 546/170
0456504-A2 11/1991 European Pat. Off. ............ 546/170

OTHER PUBLICATIONS

J. March, Advanced Organic Chemistry, 3rd Ed. pp. 805–806 (1985).

Primary Examiner—C. Warren Ivy
Assistant Examiner—Zinna N. Davis
Attorney, Agent, or Firm—Peggy A. Climenson

[57] ABSTRACT

There is provided a convenient process for the preparation of commercially useful pyridinedicarboxylate compounds by the condensation of an α, β-unsaturated oxime and an aminomaleate or aminofumarate or mixtures thereof.

14 Claims, No Drawings

PROCESS FOR THE PREPARATION OF DIALKYL 2,3-PYRIDINEDICARBOXYLATE AND DERIVATIVES THEREOF FROM AN α,β-UNSATURATED OXIME AND AN AMINOBUTENEDIOATE

BACKGROUND OF THE INVENTION

Pyridine-2,3-dicarboxylates are useful intermediates in the preparation of important herbicidal 2-(2-imidazolin-2-yl)nicotinic acids, esters and salts. Said herbicidal agents and methods for their preparation are disclosed in U.S. Pat. Nos. 4,798,619 and 4,758,667. Imidazolinyl nicotinates and derivatives thereof are highly effective herbicides at low rates of application and demonstrate selective control of noxious weeds in the presence of key economic crops and, further, exhibit exceptionally low mammalian toxicity.

Among the methods for preparing these useful pyridinedicarboxylate intermediates are those described in European Patent Application Publication Nos. 308 084 and 456 504. The importance of the pyridinedicarboxylate derivatives, particularly as essential intermediates in the manufacture of herbicidal 2-(2-imidazolin-2-yl)nicotinic acids, esters and salts, creates a significant need in the art for effective processes for their production.

Therefore, it is an object of this invention to provide a process for the preparation of a substituted or unsubstituted pyridinedicarboxylic acid ester via the single step condensation of an α, β-unsaturated oxime with an aminobutenedioate in the presence of an acid, optionally in the presence of a solvent.

Another object of the present invention is to provide a ready source of pyridinedicarboxylate compounds and derivatives of said compounds as key intermediates in the production of the herbicidal agents, 2-(2-imidazolin-2-yl)nicotinic acids, esters and salts.

These and further objects of the invention will become more apparent by the description provided hereinbelow.

SUMMARY OF THE INVENTION

The present invention provides a process for the preparation of economically important pyridinedicarboxylates of formula I

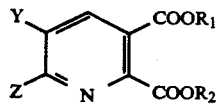
    I wherein $R_1$ and $R_2$ are each independently phenyl or $C_1$-$C_4$alkyl optionally substituted with phenyl and Y and Z are each independently hydrogen or $C_1$-$C_4$ alkyl optionally substituted with one to three halogens or $C_1$-$C_4$alkoxy groups which comprises reacting an α,β-unsaturated oxime of formula II

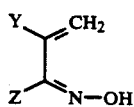
    II wherein Y and Z are described hereinabove for formula I with an aminobutenedioate of formula III

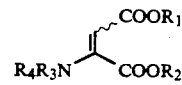
    III wherein $R_3$ and $R_4$ are each independently hydrogen, $C_1$-$C_6$alkyl, $C_3$-$C_8$cycloalkyl, phenyl or may be taken together with the atom to which they are attached to form a 5 or 6 membered alicyclic ring selected from the group consisting of pyrrolidine, piperidine and morpholine and $R_1$ and $R_2$ are as described hereinabove for formula I in the presence of an acid, optionally in the presence of a solvent at an elevated temperature.

The compounds of formula III include the aminomaleate of formula IV(a), the aminofumarante of formula IV(b) or mixtures thereof, wherein $R_1$, $R_2$, $R_3$ and $R_4$ are as described hereinabove for formula III.

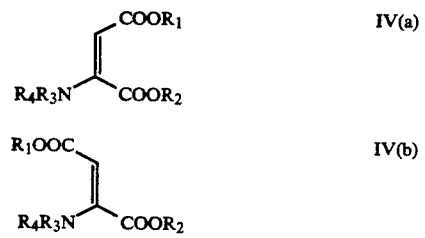

DETAILED DESCRIPTION OF THE INVENTION

Oximes of formula II may be readily prepared from the appropriate aldehyde or ketone precursor using standard literature procedures such as that reported in J. March, *Advanced Organic Chemistry, 3rd Edition*, pp. 805–806 (1985). For example, the appropriate α, β-unsaturated carbonyl compound precursor may be reacted with hydroxylamine to give the desired oxime as shown in flow diagram I.

FLOW DIAGRAM I

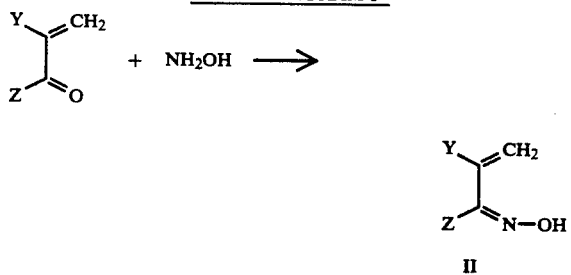

The aminobutenedioate compounds of formula III may be conveniently prepared by reacting the desired amine with a dialkyl acetylenedicarboxylate as shown in flow diagram II.

FLOW DIAGRAM II

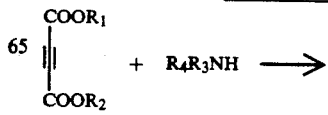

-continued
FLOW DIAGRAM II

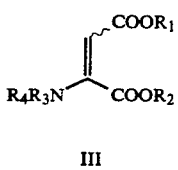

III

Alternatively, aminobutenedioates including the aminomaleate of formula IV(a) and aminofumarate of formula IV(b) may be prepared by the method described in U.S. Pat. 4,766,218.

It has now been found that 5-substituted, 6-substituted, 5,6-dicarboxylate compounds may be effectively prepared by admixing a formula I $\alpha$, $\beta$-unsaturated oxime with an aminobutenedioate of formula III, optionally in the presence of a solvent, treating this mixture with an acid and heating the resultant reaction mixture at a temperature of about room temperature to about reflux temperature. Preferably the formula I $\alpha$, $\beta$-unsaturated oxime and the aminobutenedioate of formula III are admixed at a ratio of from about 1:1 to 1:1.5 molar equivalents. The thus-formed formula I pyridinedicarboxylate product may be isolated using standard techniques such as extraction, fractional distillation, chromatography and the like. For purposes of illustration, the process is shown employing an aminobutenedioate of formula III in flow diagram III.

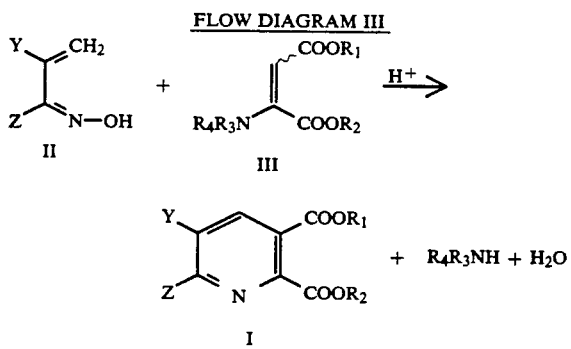

Of course, it is understood that an aminomaleate of formula IV(a), an aminofumarate of formula IV(b) as well as mixtures of aminobutenedioates may also be efficiently used in the process of the invention.

Among the acids that may be used in the process of the invention are those commonly used in condensation reactions such as acetic acid, propionic acid, p-toluenesulfonic acid, methanesulfonic acid, sulfuric acid, phosphoric acid, phosphorous oxychloride, phosphorous trichloride, phosphorous tribromide, hydrochloric acid, hydrobromic acid and the like. Preferred acids are strong mineral acids such as sulfuric, hydrochloric, hydrobromic and such. Particularly preferred is hydrochloric acid.

Solvents suitable for use in the process of the invention are aromatic hydrocarbons and haloaromatic hydrocarbons such as xylene, toluene, benzene, halobenzene, dihalobenzene and the like, haloaliphatic solvents such as dihaloethane, dihalomethane, and the like, aliphatic esters such as ethyl acetate, ethyl propionate, and so forth and alcohols such as methanol, ethanol, propanol, and the like. In general, solvents having a boiling point of about 50°–180°C. are suitable.

The rate of formation of the formula I pyridinedicarboxylate product is temperature dependent, thus, the reaction time can be effectively diminished by heating the reaction mixture at temperatures greater than room temperature, preferably at reflux temperature.

To facilitate a further understanding of the invention, the following examples are presented. The examples are primarily for the purpose of illustration of certain more specific details and the invention is not to be deemed limited thereby. Unless otherwise noted, all parts are parts by weight and the term NMR designates nuclear magnetic resonance.

EXAMPLE 1

Preparation of diethyl 5-ethyl-2,3-pyridinedicarboxylate from 2-ethylacrolein oxime and diethyl 2-aminobutenedioate

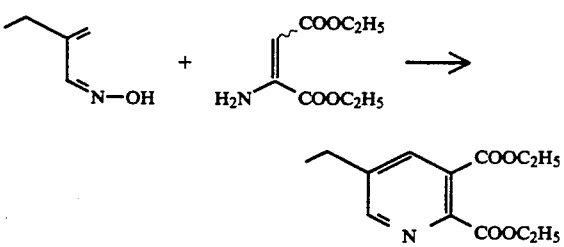

A mixture of 2-ethylacrolein oxime (4.95g, 0.05 mole) and diethyl 2-aminobutenedioate (9.35 g, 0.05 mole) in acetic acid is treated with concentrated $H_2SO_4$ (5.2 g, 0.05 mole) in a single portion at room temperature, stirred at ambient temperatures for 2.5 hours, heated at reflux temperature for 2.5 hours, cooled and concentrated in vacuo to give an oil residue. The oil residue is partitioned between ethyl acetate and water. The organic phase is concentrated in vacuo to give the title product as an oil, characterized by NMR spectroscopy.

EXAMPLE 2

Preparation of dietyl 2,3-pyridinedicarboxylate from acrolein oxime and diethyl 2-aminobutenedioate

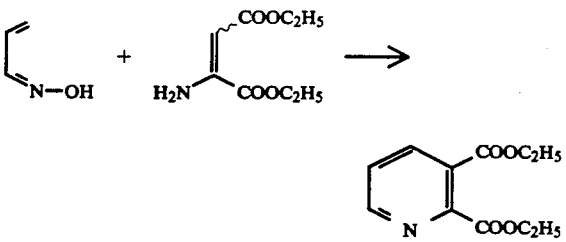

A stirred mixture of acrolein oxime (6.8 g, 0.096 mole) and diethyl 2-aminobutenedioate (9.35 g, 0.05 mole) in 25 mL of acetic acid is treated with concentrated $H_2SO_4$ (5.2 g, 0.05 mole) in a single portion to give a vigorous exotherm. The reaction mixture is heated at reflux temperature for 1 hour, cooled and concentrated in vacuo to give a tarry residue. The residue is partitioned between methylene chloride and water. The organic phase is concentrated in vacuo to give the title product as an oil, 2.4 g, 21% crude yield as determined by NMR analysis.

EXAMPLE 3

Preparation of diethyl 5 methyl 2,3 pyridinedicarboxylate from 2 methylacrolein oxime and diethyl N,N-dibutylaminobutenedioate

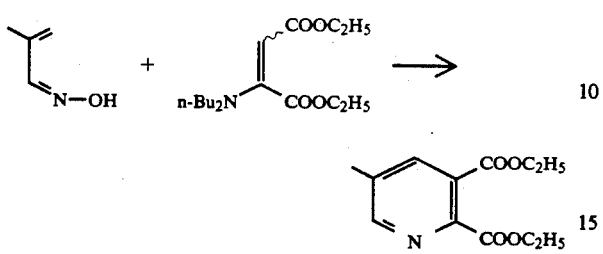

A stirred mixture of 2-methylacrolein oxime (2.21 g, 0.026 mole) and diethyl N,N-dibutylaminobutenedioate (7.8 g, 0.026 mole) in ethylenedichloride at ice bath temperatures is treated slowly with HCl gas for a 5 minute period, stirred for 1/2 hour, allowed to come to room temperature, cooled slightly to about 22° C., treated again with HCl gas until reaction mixture is homogeneous, heated at 85° C. for 2 hours, cooled to room temperature and quenched with ethyl acetate and water. The organic phase is concentrated in vacuo to give the title product as an oil residue, 6.3 g, 53% purity, 54% yield as determined by NMR analysis.

Using essentially the same procedure and employing 0.10 mole of 2-methylacrolein oxime and 0.15 mole of diethyl N,N-dibutylaminobutenedioate affords the title product in 75% yield and 53% purity as determined by NMR analysis.

EXAMPLE 4

Preparation of diethyl 5-methyl-2,3-pyridinedicarboxylate from 2-methylacrolein oxime and diethyl N-cyclohexylaminobutenedioate

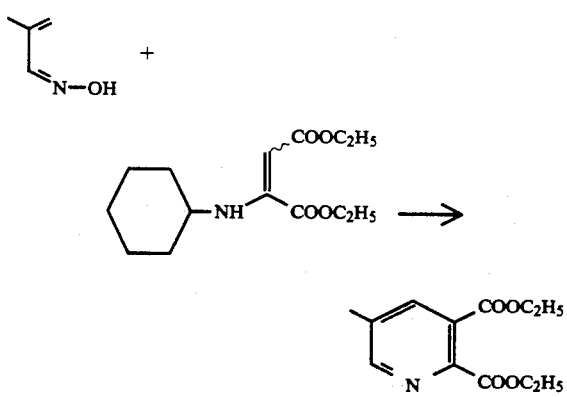

A stirred mixture of 2-methylacrolein oxime (2.13 g, 0.025 mole) and diethyl N-cyclohexylamino-butenedioate (6.3 g, 0.026 mole) in ethylene dichloride at ice bath temperatures is treated with HCl gas until exotherm is no longer observed, heated at 70°-75° C. for about 2 hours, cooled and quenched with ethyl acetate and water. The organic phase is concentrated in vacuo to give the title product as an oil residue 3.25 g, 62% crude yield, as determined by NMR analysis.

EXAMPLE 5

Preparation of diethyl 5-methyl-2,3-pyridinedicarboxylate from 2-methylacrolein oxime and diethyl morpholinobutenedioate

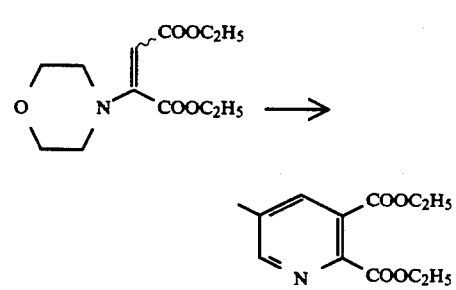

A stirred mixture pf 2-methylacrolein oxime (4.3 g, 0.05 mole) and diethyl morpholinobutenedioate (13.0 g, 0.05 mole) in ethylene dichloride is treated with HCl gas over a 10 minute period at about 25° C. (ice bath cooling) allowed to exotherm to 53° C., heated at reflux for about 1 hour, cooled and quenched with water and methylene chloride. The organic phase is concentrated in vacuo to give the title product as an oil residue, 10.6 g, 45% purity, 40% yeild as determined by NMR analysis.

I claim:

1. A process for the preparation of a compound of formula I

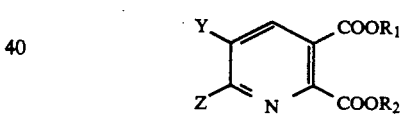

wherein
$R_1$ and $R_2$ are each independently phenyl or $C_1$-$C_4$alkyl optionally substituted with phenyl and
Y and Z are each independently hydrogen or $C_1$-$C_4$alkoxy groups
which comprises reacting an $\alpha,\beta$-unsaturated oxime of formula II

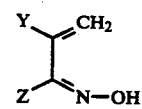

wherein Y and Z are as described above for formula I with an aminobutenedioate enamine of formula III

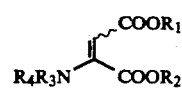

wherein
$R_3$ and $R_4$ are each independently hydrogen, $C_1$-$C_6$alkyl, $C_3$-$C_8$ Gycloalkyl, phenyl or may be taken together with the atom to which they are attached to form a 5 or 6 membered alicyclic ring selected from the group consisting of pyrrolidine, piperidine and morpholine and $R_1$ and $R_2$ are as described above for formula I, in the presence of an acid and optionally in the presence of a solvent at an elevated temperature.

2. The process according to claim 1 wherein the $\alpha,\beta$-unsaturated oxime of formula II and the aminobutenedioate of formula III are present in the ratio of about 1:1 to 1:1.5 molar equivalents.

3. The process according to claim 1 wherein the acid is selected from the group consisting of acetic acid, p-toluenesulfonic acid, methanesulfonic acid, sulfuric acid, phosphoric acid, phosphorus oxychloride, phosphorous trichloride, phosphorous tribromide, hydrogen chloride and hydrogen bromide.

4. The process according to claim 3 wherein the acid is hydrogen chloride.

5. The process according to claim 1 wherein the reaction is run in the presence of a solvent.

6. The process according to claim 5 wherein the solvent is selected from the group consisting of xylene, toluene, benzene, halobenzene, dihalobenzene, dihaloethane, dihalomethane, ethyl acetate, ethyl propionate, methanol, ethanol, propanol and butanol.

7. The process according to claim 6 wherein the solvent is dichloroethane.

8. The process according to claim 1 wherein the temperature is about 50°-180° C.

9. The process according to claim 1 for the preparation of a compound of formula I wherein Z is hydrogen and Y is $C_1$-$C_4$ alkyl optionally substituted with one halogen or $C_1$-$C_4$ alkoxy group.

10. The process according to claim 9 for the preparation of dialkyl 5-ethyl-2,3-pyridinedicarboxylate.

11. The process according to claim 9 for the preparation of dialkyl 2,3-pyridinedicarboxylate.

12. The process according to claim 9 for the preparation of dialkyl 5-methyl-2,3-pyridinedicarboxylate.

13. The process according to claim 9 for the preparation of dialkyl 5-(methoxymethyl)-2,3-pyridinedicarboxylate.

14. The process according to claim 9 for the preparation of dialkyl 5-(chloromethyl)-2,3-pyridinedicarboxylate.

* * * * *

UNITED STATES PATENT AND TRADEMARK OFFICE
CERTIFICATE OF CORRECTION

PATENT NO. : 5,227,491
DATED : July 13, 1993
INVENTOR(S) : Robert F. Doehner, Jr.

It is certified that error appears in the above-identified patent and that said Letters Patent is hereby corrected as shown below:

In Claim 1, Column 6, lines 48-49 should read as follows:

Y and Z are each independently hydrogen or $C_1$-$C_4$ alkyl optionally substituted with one to three halogen or $C_1$-$C_4$ alkoxy groups Signed and Sealed this Fifth Day of January, 1999

*Attest:*

*Attesting Officer*     *Acting Commissioner of Patents and Trademarks*